US010563253B2

(12) United States Patent
Egan et al.

(10) Patent No.: US 10,563,253 B2
(45) Date of Patent: Feb. 18, 2020

(54) CARTRIDGE INTERFACE MODULE

(71) Applicants: LOCKHEED MARTIN CORPORATION, Bethesda, MD (US); ZYGEM CORPORATION LTD., Hamilton (NZ)

(72) Inventors: Michael Edward Egan, Bothell, WA (US); Orion N. Scott, Charlottesville, VA (US); James Landers, Charlottesville, VA (US); Douglas J. South, Rockville, MD (US); Brian E. Root, Charlottesville, VA (US)

( * ) Notice: Subject to any disclaimer, the term of this patent is extended or adjusted under 35 U.S.C. 154(b) by 0 days.

(21) Appl. No.: 16/270,218

(22) Filed: Feb. 7, 2019

(65) Prior Publication Data
US 2020/0002745 A1    Jan. 2, 2020

Related U.S. Application Data

(63) Continuation of application No. 14/227,645, filed on Mar. 27, 2014, now abandoned.

(60) Provisional application No. 61/805,729, filed on Mar. 27, 2013.

(51) Int. Cl.
*C12Q 1/686* (2018.01)

(52) U.S. Cl.
CPC .................. *C12Q 1/686* (2013.01)

(58) Field of Classification Search
CPC ................................ C12Q 1/686
See application file for complete search history.

(56) References Cited

U.S. PATENT DOCUMENTS 5,922,591 A    7/1999    Anderson

FOREIGN PATENT DOCUMENTS

| WO | WO 2008055257 A2 | 5/2008 |
| WO | WO 2008080106 A1 | 7/2008 |

*Primary Examiner* — Michael J Felton
*Assistant Examiner* — Katherine A Will
(74) *Attorney, Agent, or Firm* — Oblon, McClelland, Maier & Neustadt, L.L.P.

(57) ABSTRACT

A cartridge interface module (CIM), configured to engage with a removable microfluidic cartridge in a nucleic acid analyzer system can include a fluidics component, which is configured to initiate and support a liquid extraction of nucleic acids from a biological sample contained in the removable microfluidic cartridge. The CIM also includes a polymerase chain reaction (PCR) assembly component which can be configured to initiate and support amplification of the extracted nucleic acids. The CIM may also include a high voltage electrodes component that is configured to initiate and support separation of the amplified nucleic acids into nucleic acid fragments in a separation channel of the removable microfluidic cartridge. The CIM also includes a detection optics component that can be configured to collect, detect, and direct label nucleic acid fragments. The CIM is configured to integrate with a microfluidic chip architecture of an inserted removable microfluidic cartridge.

7 Claims, 14 Drawing Sheets

Receiving a removable microfluidic cartridge into a cartridge interface module (CIM) of a nucleic acid analyzer system
1610

Initiating and supporting extraction of nucleic acids from the biological sample contained within the removable microfluidic cartridge, via a fluidics component of the CIM while engaged with the removable microfluidic cartridge
1620

Initiating and supporting amplification of the extracted nucleic acids, via a polymerase chain reaction (PCR) assembly component of the CIM while engaged with the removable microfluidic cartridge
1630

Initiating and supporting separation of the amplified nucleic acids into nucleic acid fragments, via a high voltage electrodes component of the CIM while engaged with a separation channel of the removable microfluidic cartridge
1640

Directing an input light beam to a separation channel for detection and collection of the nucleic acid fragments, via a detection optics component
1650

CARTRIDGE INTERFACE MODULE

CROSS-REFERENCE TO RELATED APPLICATION

This application is a continuation application of U.S. application Ser. No. 14/227,645 filed Mar. 27, 2014, the entire contents of which are incorporated herein by reference. U.S. application Ser. No. 14/227,645 claims the benefit of U.S. Provisional Application No. 61/805,729, filed on Mar. 27, 2013, the disclosure of which is incorporated in its entirety by reference herein.

BACKGROUND

Genetic testing is used for various purposes, including forensic/identity testing, paternity testing, diagnostic testing, disease screening, environmental monitoring, food safety etc. Genetic testing relies on being able to analyze nucleic acids in a biological sample. Accordingly, improvements in nucleic acid analysis will further enhance the utility of genetic testing. In human identification-applications of genetic testing, such as forensic applications, nucleic acid analysis can be used to provide near certain matching of a biological sample to a person.

SUMMARY

In embodiments, a cartridge interface module (CIM), configured to engage with a removable microfluidic cartridge in a nucleic acid analyzer system can include a fluidics component, which is configured to initiate and support a liquid extraction of nucleic acids from a biological sample contained in the removable microfluidic cartridge. The CIM also includes a polymerase chain reaction (PCR) assembly component, which is configured to initiate and support amplification of the extracted nucleic acids. The CIM can also include a high voltage electrodes component, which is configured to initiate and support separation of the amplified nucleic acids into nucleic acid fragments in a separation channel of the removable microfluidic cartridge. The CIM also includes a detection optics component, which is configured to detect labeled nucleic acid fragments. The CIM is configured to integrate with a microfluidic chip architecture of an inserted removable microfluidic cartridge for execution of the extraction, amplification, and separation of the biological sample within the removable microfluidic cartridge.

In embodiments, a method of analyzing a biological sample for DNA analysis can include receiving a removable microfluidic cartridge into a CIM of a nucleic acid analyzer system. The method also includes initiating and supporting extraction of nucleic acids from the biological sample contained within the removable microfluidic cartridge, via a fluidics component of the CIM while engaged with the removable microfluidic cartridge. The method can also include initiating and supporting amplification of the extracted nucleic acids, via a polymerase chain reaction assembly component of the CIM while engaged with the removable microfluidic cartridge. The method may also include initiating and supporting separation of the amplified nucleic acids into nucleic acid fragments, via a high voltage electrodes component of the CIM while engaged with a separation channel of the removable microfluidic cartridge. The method also includes directing an input light beam into a separation channel for detection and collection of the nucleic acid fragments, via a detection optics component of the CIM.

In embodiments, a CIM of a nucleic acid analyzer system may include a fluidics component, a high voltage electrode component, a pneumatic connector component, a cartridge support component, a microfluidic valve actuator component, a liquid extraction heater component, a detection optics component, a stage heater component, and a polymerase chain reaction component. The components of the CIM are configured to integrate with a microfluidic chip architecture of an inserted removable microfluidic cartridge to extract, amplify, and separate a biological sample within the removable microfluidic cartridge.

BRIEF DESCRIPTION OF THE DRAWINGS

Various exemplary embodiments will be described in detail with reference to the following figures, wherein:

FIG. 16 is a flow chart illustrating an exemplary process of analyzing a biological sample.

DETAILED DESCRIPTION

Figure 1:
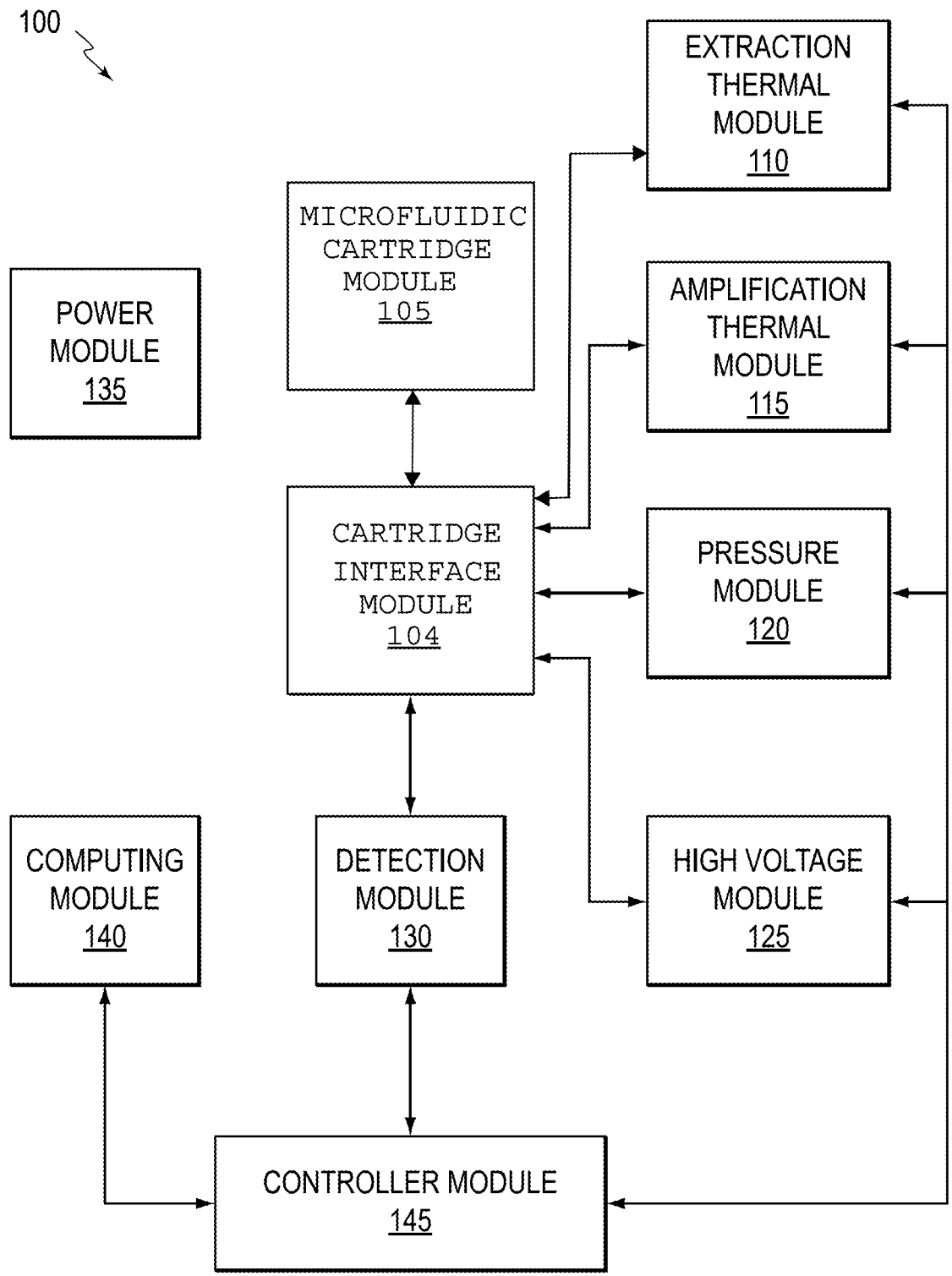
FIG. 1 is a block diagram of an exemplary nucleic acid analyzer.

FIG. 1 shows a block diagram of an exemplary nucleic acid analyzer 100. As shown, the nucleic acid analyzer 100 can include a microfluidic cartridge module 105, a cartridge interface module 104, an extraction thermal module 110, an amplification thermal module 115, a pressure module 120, a high voltage module 125, a detection module 130, a power module 135, a computing module 140, and a controller module 145. The modules can be operably connected as shown in FIG. 1. In embodiments, the modules can also be combined or more than one of each module may be present in a nucleic acid analyzer.

The nucleic acid analyzer 100 is capable of performing nucleic acid analysis using a microfluidic cartridge. The nucleic acid analyzer 100 can be operated to perform nucleic acid analysis by a user without the need for substantial experience with and knowledge of the processes used to perform nucleic acid analysis. For example, the appropriate procedures for using the nucleic acid analyzer 100 can be learned in an hour or less. The nucleic acid analyzer 100 is designed to use liquid volumes on the order of micro-liters or less. By using micro-liter liquid volumes, nucleic analysis can be performed in reduced time as compared to time-intensive nucleic acid analysis currently in use. In embodiments, nucleic acid analysis can be performed in less than two hours.

The microfluidic cartridge module 105 is configured to accept one or more microfluidic cartridges (not shown). The cartridge interface module 104 is configured to operably couple the microfluidic cartridge module 105 to the other modules. In an embodiment, some of the other modules, such as the detection module 130, the extraction thermal module, the amplification thermal module 115, and the like, can be integrated in the cartridge interface module 104. The microfluidic cartridge can include a micro-to-macro interface and features that allow the microfluidic cartridge to be acted upon by other components of the nucleic acid analyzer 100. The microfluidic cartridge can be a disposable cartridge, such as a single-use cartridge. In general, microfluidic cartridges can include various features for performing any of nucleic acid extraction, nucleic acid amplification, and nucleic acid separation. Defined within the microfluidic cartridge is a fluidic network formed from fluidic channels, fluidic chambers and/or reservoirs, and other features for performing nucleic acid extraction, nucleic acid amplification, and/or nucleic acid separation. The microfluidic cartridge can be constructed from any suitable material. As examples, the microfluidic cartridge can be constructed from a plastic, polymeric material, glass, and the like. Additionally, the microfluidic cartridge can be constructed from multiple types of materials.

The extraction thermal module 110 is configured to impart suitable temperatures for nucleic acid extraction. The extraction thermal module 110 can be controlled by the controller module 145. The extraction thermal module 110 can be coupled to a cartridge or a sample acceptor during nucleic acid extraction. The extraction thermal module 110 can perform contact and/or non-contact thermal heating. In an example, the extraction thermal module 110 includes one or more contact heating units. Heating with the extraction thermal module can facilitate the extraction of nucleic acids with thermophilic enzymes.

The amplification thermal module 115 is configured to impart suitable temperatures to the microfluidic cartridge during nucleic acid amplification. The amplification thermal module 115 can be controlled by the controller module 145. In embodiments, the amplification thermal module 115 can be configured to impart thermal gradients and perform temperature sensing in a thermal cycling process in an amplification chamber of the microfluidic cartridge. The amplification thermal module 115 can perform contact and/or non-contact thermal heating. In an example, the amplification thermal module 115 includes a non-contact heating unit, such as an infrared light source. The infrared light source can be a halogen light bulb. Further, the amplification thermal module 115 can include a temperature sensing unit. In an embodiment, the temperature sensing unit is an infrared pyrometer that measures blackbody radiation to determine the temperature of a selected portion of the microfluidic cartridge. Further, in embodiments, a single thermal module can be configured to impart temperature changes for both extraction and amplification, as necessary, using the same heating means.

The pressure module 120 is operably coupled to the microfluidic cartridge by, for example, the micro-to-macro interface. The pressure module 120 can be controlled by the controller module 145. The pressure module 120 is configured to provide pressures and/or vacuums (i.e., positive and/or negative pressures) to the microfluidic cartridge to move fluid within a fluidic network of the microfluidic cartridge. In other words, the pressure module 120 can effectuate hydrodynamic movement using, for example, pneumatic pressure in the microfluidic cartridge. In an embodiment, the pressure module 120 is coupled to one or more clusters of vent ports on the microfluidic cartridge at the micro-to-macro interface. The pressure module 120 can connect a solenoid manifold to the plurality of vent ports of the microfluidic cartridge at the micro-to-macro interface. The pressure module 120 can impart pressure to each vent port independently to move fluid through the fluidic network in the microfluidic cartridge. In an embodiment, the microfluidic cartridge has one or more valves that are configured to be actuated by the pressure module 120. The pressure module 120 can include a pressure/vacuum system, such as a pneumatic pressure/vacuum system, to suitably control hydrodynamic movement in the fluidic network of the microfluidic cartridge.

The power module 135 generates various operation powers for various components of the nucleic acid analyzer 100. In an example, the nucleic acid analyzer 100 is implemented using a modular design. Each module of the nucleic acid analyzer 100 requires an operation power supply, which can be different from the other modules. The power module 135 can receive an AC power input, such as 100-240 V, 50-60 Hz, single phase AC power from a power outlet. The power module 135 can use the AC power input to generate 5 V, 12 V, 24 V, and the like, to provide operation powers for the various components of the nucleic acid analyzer 100. In other embodiments, the power module 135 can be a battery.

The power module 135 also imparts power to the high voltage module 125 as required for nucleic acid processes on the microfluidic cartridge, such as electrophoretic separation. The power module 135 can implement various protective functions, such as power outage protection, graceful shut-down, and the like, to protect the various components and data against power failure. In an embodiment, the power module 160 includes a back-up power, such as a battery module, to support one or more protective functions, such as graceful shut-down.

The high voltage module 125 receives power from the power module 135 and generates high voltages such as 1000 V, 2000 V, and the like, required for nucleic acid processes on the microfluidic cartridge, such as electrophoretic separation. The high voltage module 125 can apply the high voltages to the microfluidic cartridge under control of the controller module 145. For example, the high voltage module 125 includes an interface that applies the high voltages to electrodes on the microfluidic cartridge to induce electrokinetic injection and/or electrophoretic separation.

The detection module 130 includes components configured to detect labeled or dyed nucleic acids. The detection module 130 can be controlled by the controller module 145. In an embodiment, the detection module 130 is configured for fluorescence detection, such as multicolor fluorescence detection. The detection module 130 can include a laser source unit, an optical unit, and a detector unit. The optical unit includes a set of optics. In an embodiment, the optical unit includes a self-calibrating array of confocal optical components. The laser source unit emits a laser beam. In an example, the laser source unit includes an argon-ion laser unit. In another example, the laser source unit includes a solid state laser, such as a coherent sapphire optically pumped semiconductor laser unit. The solid state laser has the advantages of reduced size, weight and power consumption.

In operation, the set of optics can direct the laser beam to penetrate a detection region of a separation channel in the microfluidic cartridge. The laser beam can excite fluorescent molecules attached to nucleic acids to emit fluorescence. The set of optics can then collect and direct the emitted fluorescence to the detector unit for detection. The detector unit can convert the detected fluorescence into data for subsequent processing by the computing module 140. An exemplary detection technique is disclosed by co-pending U.S. application Ser. No. 13/273,947 entitled, "Micro Fluidic Optic Design," which is hereby incorporated herein by reference in its entirety.

The computing module 140 includes computing and communication units. The computing module 140 is operably coupled to the controller module 145. The computing module 140 can provide a user interface. The user interface can provide the status of the nucleic acid analyzer 100 and can receive user instructions for controlling the operation of the nucleic acid analyzer 100. The computing module 140 includes various storage media to store software instructions and data. The computing module 140 can include nucleic analysis software that can perform data processing based on raw data obtained from the detection module 130. In addition, the computing module 140 can be coupled to external processing units, such as a database, a server, and the like to further process the data obtained from nucleic acid analysis.

The controller module 145 can receive status signals and feedback signals from the various components and provide control signals to the various components according to a nucleic acid analysis procedure. In addition, the controller module 145 can provide the status signals to the computing module 140 to inform a user of the status of nucleic acid analysis. Further, the controller module 145 can receive user instructions from the computing module 140 and can provide control signals to the various components based on user instructions.

Figure 2:
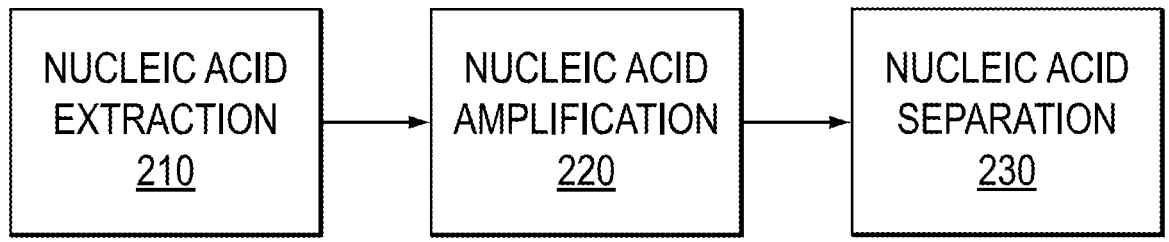
FIG. 2 is a conceptual diagram of the functions performed by embodiments of the microfluidic cartridge.

FIG. 2 shows a conceptual diagram of the functions performed by embodiments of the microfluidic cartridge. The microfluidic cartridge includes various features for performing nucleic acid extraction 210, nucleic acid amplification 220, and/or nucleic acid separation 230. Nucleic acids include DNA and RNA. In an example, extraction, amplification, and separation are performed solely to analyze DNA. In another example, RNA is analyzed by, for example, extracting RNA, reverse transcribing RNA and amplifying the resulting cDNA, and separating the DNA. Importantly, in embodiments, no additional purification feature is required between features for performing nucleic acid extraction 210 and nucleic acid amplification 220.

Nucleic acid extraction 210 is performed on a biological sample. Examples of biological samples that contain nucleic acids include saliva, blood, fecal, and urine samples. To extract the nucleic acids from the biological sample, other components of the cell must be inactivated and/or degraded. Nucleic acid extraction 210 can be carried out by contacting the biological sample with an enzymatic mixture. The enzymatic mixture can be a liquid-phase mixture. The enzymatic mixture can enzymatically digest proteins and other cellular interferences in the biological sample, with the exception of nucleic acids. In an embodiment, the enzymatic mixture includes thermostable proteinases. The thermostable proteinases can be from thermophilic Bacillus species. For example, a liquid phase mixture including thermostable proteinases from thermophilic Bacillus species is disclosed in U.S. Patent Application Publication No. 2004/0197788, which is incorporated herein by reference in its entirety. In an embodiment, the enzymatic mixture performs nucleic acid extraction when a sample collection portion (e.g., in the form of a swab) of a sample acceptor holding a biological sample is contacted by the enzymatic mixture. In an example, a final nucleic acid concentration of the resulting extracted nucleic acid mixture is in a range of 0.5-20 ng/μL.

Nucleic acid extraction 210 can be followed by nucleic acid amplification 220 without additional treatment of the extracted nucleic acid mixture. Specifically, a portion of the extracted nucleic acid mixture can be mixed with amplification reagents to perform nucleic acid amplification 220 without additional purification steps. The enzymatic nucleic acid extraction procedure described herein can generate sufficiently clean nucleic acid solutions to proceed with amplification. The nucleic acid solutions may contain species that are sufficiently broken down so that they do not interfere with subsequent reactions.

Nucleic acid amplification 220 can follow nucleic acid extraction 210. Nucleic acid amplification 220 is performed on template nucleic acid regions (sequences) in an extracted nucleic acid mixture. Nucleic acid amplification 220 can be performed by polymerase chain reaction (PCR), among other amplification techniques. To perform PCR, DNA having one or more template regions is mixed with suitable PCR reagents. PCR reagents include a DNA polymerase, nucleotides, and primers (oligonucleotides) that contain sequences complementary to the template DNA sequences. The polymerase enzymatically produces a new DNA strand from the template DNA by using the template DNA to guide synthesis of the new DNA strand through the extension of the primers by incorporating nucleotides at the end of the primers. The primers can be tagged with labels to generate labeled synthesized DNA strands after amplification. In other embodiments, the synthesized DNA strands can be tagged with labels during PCR by, for example, using labeled nucleotides to synthesize the DNA strands. The labels can be fluorescent labels. Fluorescents labels emit fluorescence of known wavelengths when excited by a laser beam. PCR requires thermal cycling. Thermal cycling is the repeated heating and cooling of the PCR mixture, including the PCR reagents and template DNA. Thermal cycling is conducted to melt the DNA, hybridize the primers to the template DNA, and to perform enzymatic replication of the template DNA regions. As PCR progresses, the DNA generated is itself used as template DNA for replication in succeeding cycles. Thus, PCR is a chain reaction that exponentially amplifies the template DNA regions. Amplification results in an amplified nucleic acid mixture.

Nucleic acid separation 230 can follow nucleic acid amplification 220. Nucleic acid separation 230 is performed to separate nucleic acid fragments in a nucleic acid mixture, such as an amplified nucleic acid mixture, and can enable detection and analysis of the nucleic acid fragments. In embodiments, electrophoresis can be used to separate the nucleic acid fragments by size. In electrophoresis, nucleic acid fragments are subjected to an electric field to force the nucleic acid fragments through a sieving medium. The nucleic acid fragments migrate by force of the electric field at different speeds based on size. An electric field induces a nucleic acid fragment to migrate due to the net negative charge of the sugar-phosphate backbone of the nucleic acid fragment. The sieving medium can be a polymer matrix formed from a polymer solution. As examples for forming such a matrix, suitable polymer solutions are disclosed in U.S. Pat. Nos. 8,207,258, 8,017,682, 7,862,699, 7,531,073, 7,399,396, 7,371,533, 7,026,414, 6,811,977 and 6,455,682, which are incorporated herein by reference in their entireties. In an example, a sieving polymer matrix can be used to yield single-base resolution. During or after separation, the DNA fragments can be detected and analyzed.

Figure 3:
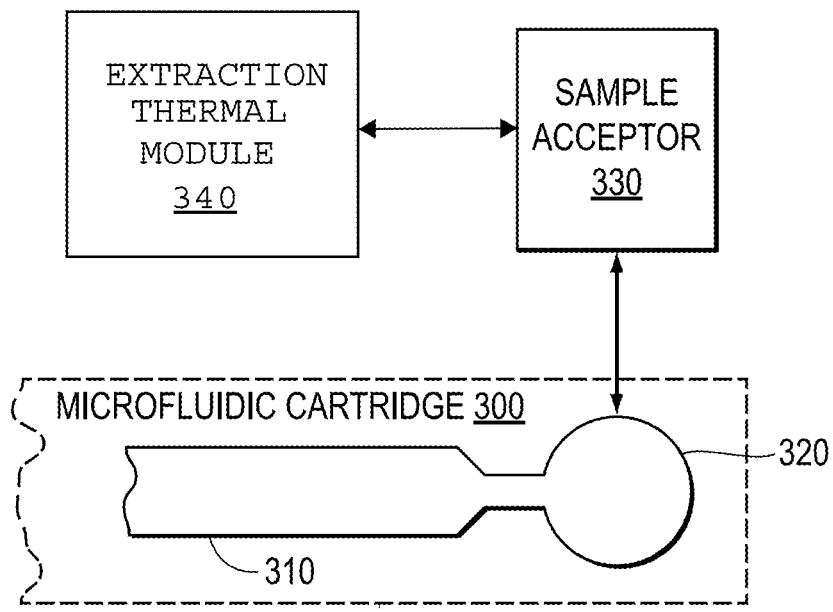
FIG. 3 shows exemplary features for performing nucleic acid extraction.

FIG. 3 shows exemplary features for performing nucleic acid extraction that can be included within a microfluidic cartridge 300. As shown, the microfluidic cartridge 300 can be provided with an extraction mixture reservoir 310 in fluid communication with a sample input 320. Other features for performing nucleic acid extraction may be provided off-cartridge. In an embodiment, the off-cartridge features include a sample acceptor 330 and an extraction thermal module 340. In an example, the sample acceptor 330 and the extraction thermal module 340 are coupled together. The extraction mixture reservoir 310 is configured to hold the enzymatic mixture for performing nucleic acid extraction. In embodiments, the extraction mixture reservoir is configured to hold from about 25 µl to about 500 such as from about 200 µl to about 250 µl or about 225 µl, of the enzymatic mixture. The enzymatic mixture is provided to or pre-loaded in the extraction mixture reservoir 310.

In use, the sample acceptor 330 is coupled with the sample input 320 such that the extraction mixture reservoir 310, the sample input 320, and the sample acceptor 330 are in fluid communication. The sample acceptor 330 presents a previously-collected biological sample for nucleic acid extraction. In embodiments, the minimal amount of biological material required to be presented is about 100 cells. The enzymatic mixture can be provided from the extraction mixture reservoir 310 to the sample acceptor 330 in order to initiate nucleic acid extraction. To aid enzymatic digestion, the enzymatic mixture can be moved in a back-and-forth motion within the sample acceptor 330 and the extraction mixture reservoir 310. The extraction thermal module 340 can heat the enzymatic mixture to promote enzymatic digestion of cellular components other than nucleic acids. Extraction can be performed at a first temperature. Enzymes of the enzymatic mixture can be inactivated at a second higher temperature to conclude nucleic acid extraction. In an example, nucleic acid extraction is performed at 75° C. for 10 minutes to extract the nucleic acids through enzymatic digestion. Then, the heat is increased and held at 95° C. to inactivate the enzymes in the enzymatic mixture. In such an example, the enzymes include thermostable proteinases that functional at 75° C., but that are inactivated at higher temperatures, such as 95° C. Upon completion of enzymatic digestion, the resulting extracted nucleic acid mixture can be received by and stored in the extraction mixture reservoir 310 for further processing. The extraction mixture reservoir 310 can have one or more fluidic channels (not shown) branching from the extraction mixture reservoir 310 to provide the extracted nucleic acid mixture to other portions of the microfluidic cartridge through a fluidic network.

Figure 4:
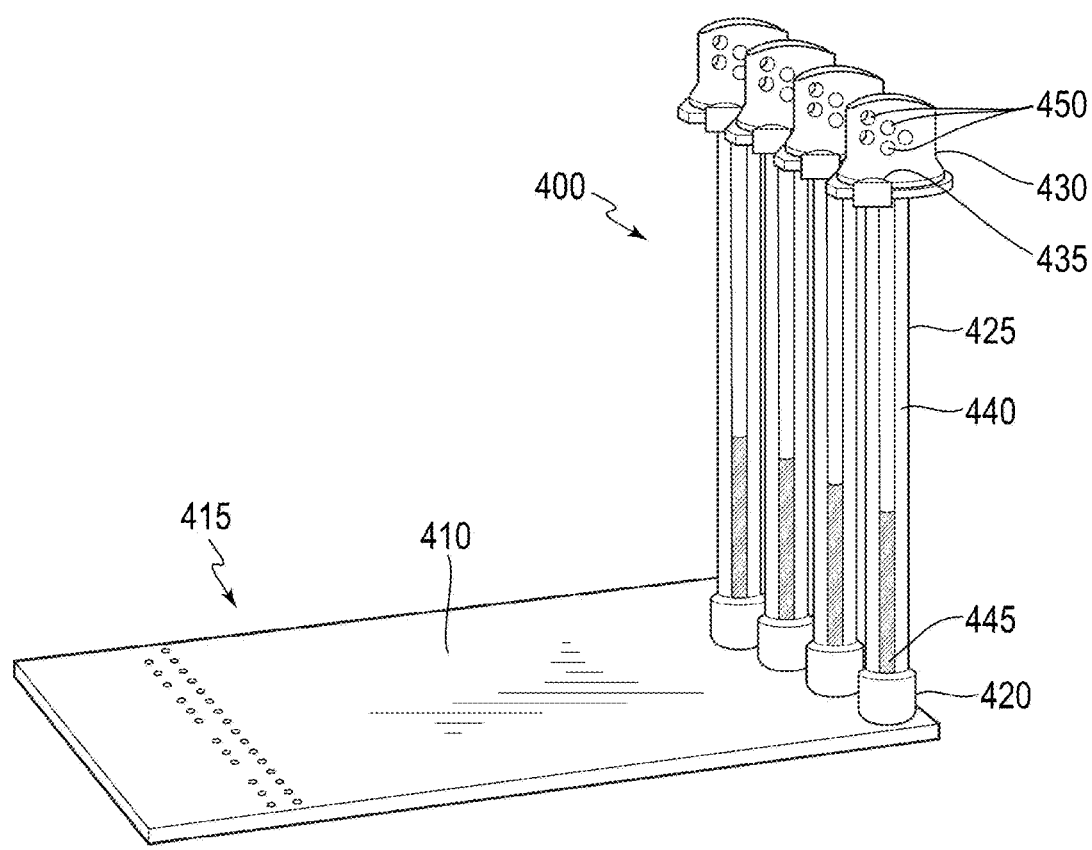
FIG. 4 shows a plurality of exemplary sample acceptors fluidically coupled to an exemplary microfluidic cartridge.
Figure 5:
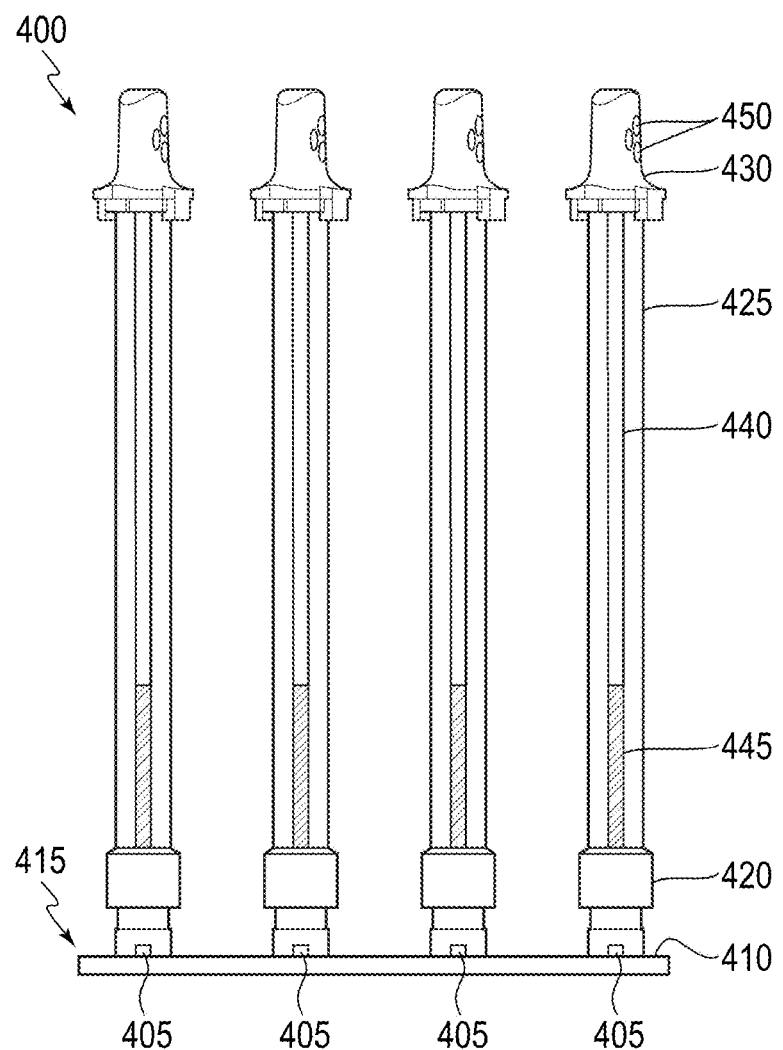
FIG. 5 shows another view of the plurality of exemplary sample acceptors fluidically coupled to the exemplary microfluidic cartridge shown in FIG. 4.

FIGS. 4 and 5 show a plurality of exemplary sample acceptors 400 fluidically coupled to a plurality of exemplary sample inputs 405 formed on an outer surface 410 of an exemplary microfluidic cartridge 415. As shown, each sample input 405 includes a portion surrounding an opening that protrudes from the outer surface 410 of the microfluidic cartridge 415. In FIGS. 4 and 5, four sample acceptors 400 are fluidically coupled to four sample inputs 405 of the microfluidic cartridge 415. In other embodiments, the microfluidic cartridge 415 can include less than four sample inputs 405, including a single sample input 405, or more than four sample inputs 405 for fluidically coupling the same number of sample acceptors 400. The sample inputs 405, as well as the sample acceptors 400, can be of the same or different types. As shown, the sample acceptors 400 and the sample inputs 405 are of the same type. Alternatively, one or more of the sample acceptors 400 and the sample inputs 405 can be of different types.

As further shown, each sample acceptor 400 includes an input-matable portion 420, an acceptor portion 425, and a detachable portion 430 for sample collection. The input-matable portion 420 is at one end of the acceptor portion 425. The acceptor portion 425 is in the form of a barrel similar to a syringe barrel. The input-matable portion 420 can be configured to be coupled to the sample input 405 to form a fluid-tight seal. The input-matable portion 420 and the sample input 405 can be based on any small-scale fluid fitting system. In embodiments, the input-matable portion 420 and the sample input 405 each have a universal connector selected from the group consisting of Luer-Lok connectors, threaded connectors, and flanged connectors. For example, the input-matable portion 420 and the sample input 405 can be based on a Luer-Lok fitting system. In an embodiment, the sample input 405 is threaded such as to be a female Luer-Lok fitting and the input-matable portion 420 is based on a complementary male Luer-Lok fitting that has an inner flange configured to fit inside the opening of the sample input 405 and a second outer flange that is threaded and configured to be screw-fitted onto the threaded sample input 405.

The detachable portion 430 is configured to be removed from the acceptor portion 425 to collect a biological sample and again coupled to the acceptor portion 425 after collection of the biological sample has been completed. To effectuate removable coupling, the detachable portion 430 includes a flanged grip 435. The flanged grip 435 can be configured to be reversibly coupled to a complementary end of the acceptor portion 425. Extending from the flanged grip 435 is an elongated member 440 that includes a sample collection portion 445. The sample collection portion 445 can be in the form of a swab.

Nucleic acid extraction can be performed when the microfluidic cartridge 415 is coupled to a pressure module of a nucleic acid analyzer. The pressure module can provide positive and/or negative pressure to force an enzymatic mixture from an extraction mixture reservoir of the microfluidic cartridge 415 into the sample acceptor 400 in order to perform nucleic acid extraction on a biological sample presented by the sample acceptor 400. To aid enzymatic digestion, the pressure module, through positive and/or negative pressure, can move the enzymatic mixture in a back-and-forth motion within the sample acceptor 400 and the extraction mixture reservoir of the microfluidic cartridge 415. The flanged grip 435 of the sample acceptor 400 can be gas permeable to permit gas (e.g., air) to exit the sample acceptor 400. As shown, the sample acceptor 400 is made gas permeable by including openings 450 defined in the flanged grip 435.

The microfluidic cartridge 415 can include a vent port in fluid communication with the extraction mixture reservoir, which can place the pressure module in serial fluid communication with the sample acceptor 400 through the extraction mixture reservoir and the sample input 405. In embodiments, the pressure module applies positive and/or negative pressure to the distal end of the extraction mixture reservoir to force a volume of the enzymatic mixture through the sample input 405 into the sample acceptor 400, where the enzymatic mixture can submerge the biological sample presented on the sample collection portion 445 of the sample acceptor 400. The pressure module, under control of a controller module, can then force the enzymatic mixture and dissolved biological sample back into the extraction mixture reservoir. The pressure module can revert at least a major portion of the enzymatic/biological sample mixture back into the sample acceptor 400. This back-and-forth motion can be continued by operation of the pressure module using positive and/or negative pressure, such as pneumatic pressure, and discontinued once nucleic acid extraction is completed. The turbidity associated with the back-and-forth motion can aid nucleic acid extraction and can produce a well-mixed solution of extracted nucleic acids.

During nucleic acid extraction, the sample acceptor 400 can be coupled to an extraction thermal module of a nucleic acid analyzer. As discussed above, the extraction thermal module can heat the enzymatic mixture to promote enzymatic digestion of cellular components (other than nucleic acids) of the biological sample presented by the sample acceptor 400.

Figure 6:
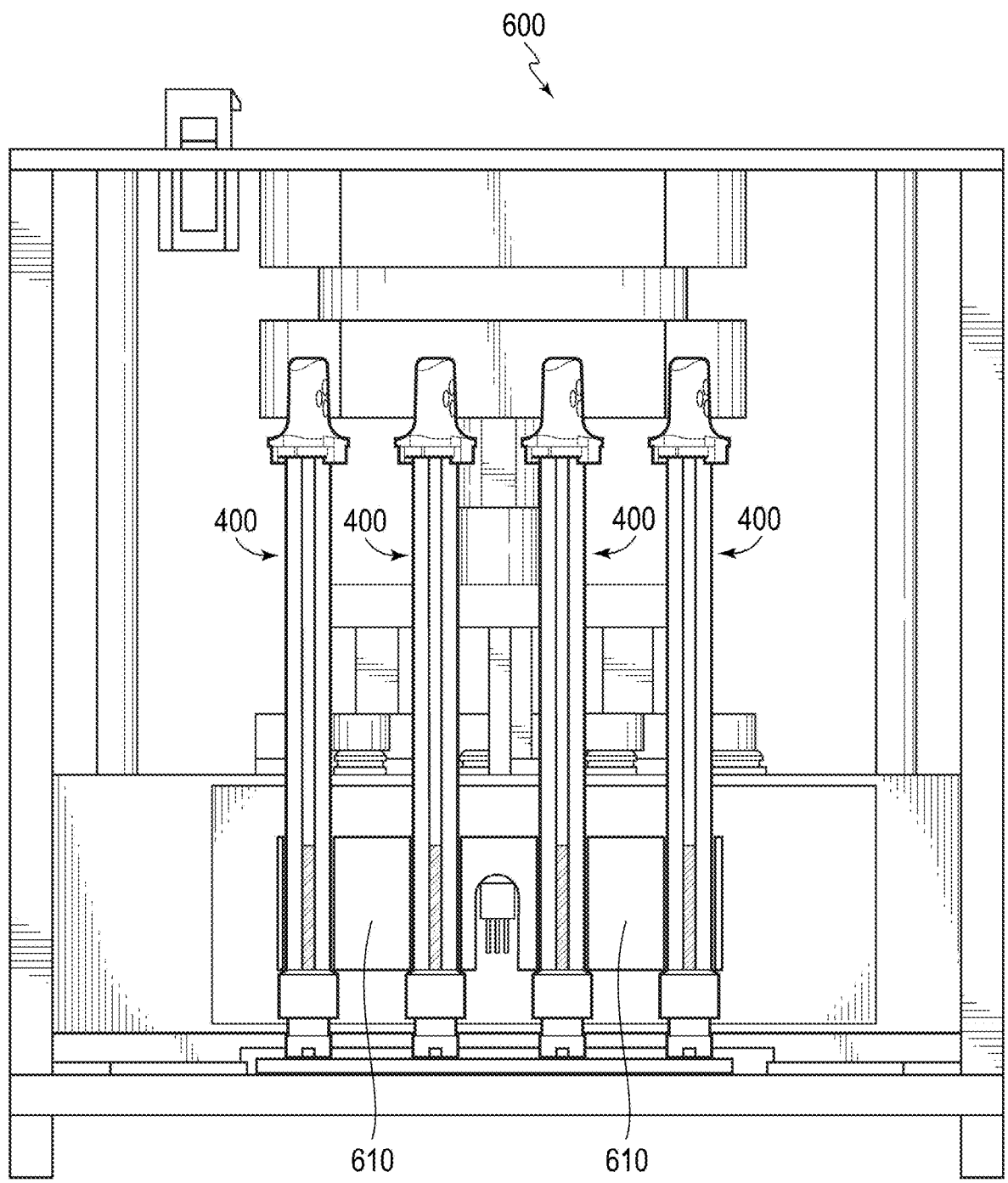
FIG. 6 shows a portion of an exemplary nucleic acid analyzer that includes an extraction thermal module.

FIG. 6 shows a portion of an exemplary nucleic acid analyzer 600 that includes an extraction thermal module 610. As shown, sample acceptors 400 are received by the nucleic acid analyzer 600 such that they are operably coupled to the extraction thermal module 610. The extraction thermal module 610 can heat the sample acceptors 400 by contact heating.

Figure 7:
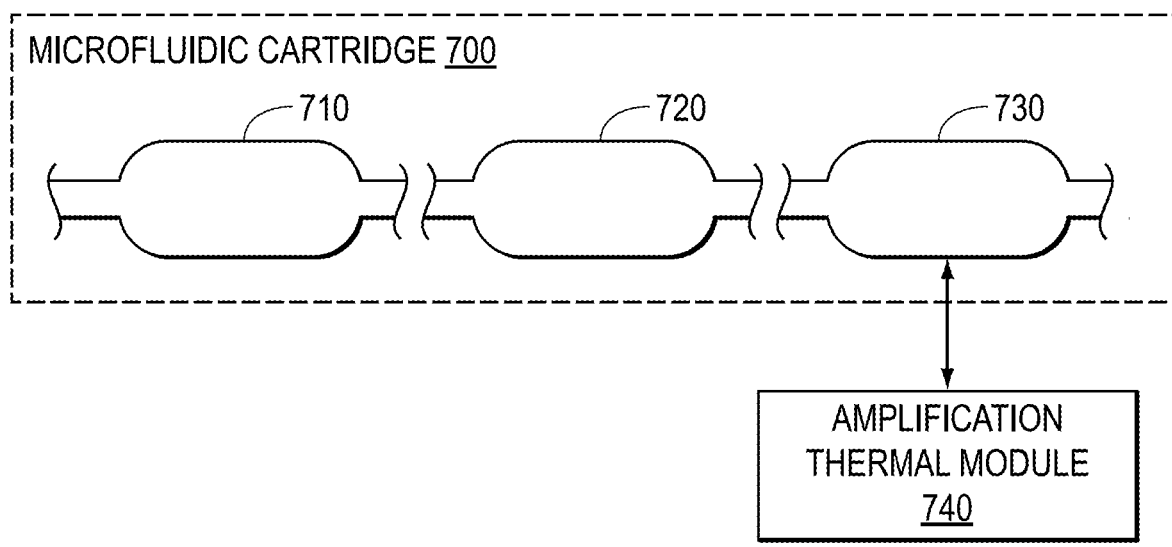
FIG. 7 shows exemplary features for performing nucleic acid amplification.

FIG. 7 shows exemplary features for performing nucleic acid amplification on template nucleic acid regions in an extracted nucleic acid mixture. As shown, on-cartridge features included within a microfluidic cartridge 700 include an amplification reagent reservoir 710, a mixing chamber 720, and an amplification chamber 730. In this example, the amplification reagent reservoir 710, the mixing chamber 720, and the amplification chamber 730 are in serial fluid communication. However, other types of fluid communication are possible. The amplification reagent reservoir 710 holds amplification reagents for performing a nucleic acid amplification reaction. In an embodiment, the amplification reagents are PCR reagents, including a DNA polymerase, nucleotides, and primers. The amplification reagents can be contained in more than one amplification reagent reservoir 710. In an embodiment, the DNA polymerase is contained in a separate amplification reagent reservoir 710 from the primers and nucleotides.

During operation, the amplification reagents are provided to the mixing chamber 720. A portion of an extracted nucleic acid mixture is also provided to the mixing chamber 720. In this embodiment, the extracted nucleic acid mixture portion is provided to the mixing chamber 720 using the same fluidic channel as used to provide the amplification reagents to the mixing chamber 720. In embodiments, the extracted nucleic acid mixture portion is from about 1 µl to about 50 µl, such as from about 25 µl to about 35 µl or about 30 µl. The extracted nucleic acid mixture portion can be mixed with the amplification reagents in a ratio of from 0.1:1 to 1:1 or from 1:1 to 1:0.1 depending on the concentrations of the reagents. The total volume of the extracted nucleic acid mixture portion and the amplification reagents can be from about 25 µl to about 100 µl. The extracted nucleic acid mixture portion and the amplification reagents can be prevented from mixing until they reach the mixing chamber 720 by moving the extracted nucleic acid mixture portion and the amplification reagents in discrete volumes. The discrete volumes can be physically separated. For instance, because the extracted nucleic acid mixture portion and the amplification reagents are in liquid volumes, the liquid volumes can be kept physically separate by moving another fluid, such as air, in between the liquid volumes. In an alternative embodiment, the extracted nucleic acid mixture portion can be provided to the mixing chamber using a different fluidic channel.

In the mixing chamber 720, the extracted nucleic acid mixture portion containing the extracted nucleic acids and the amplification reagents are mixed. The mixing chamber 720 can hold a total solution volume greater than the total solution volume to be introduced. This design allows space for air bubbles to rise from the fluid surface to the top of the chamber and the contained gas (e.g., air) can escape through a fluidically-coupled vent. The dimensions of the mixing chamber 720 can be further optimized for the escape of bubbles. For example, the vent can be configured on the opposite end of an elongated, chamber from the input channels where fluid is introduced. The input channels in fluid communication with the mixing chamber 720 may be in a perpendicular orientation to the long side of the mixing chamber 720 so as to promote turbidity among the introduced fluids. In other words, the mixing chamber 720 can be configured to have a liquid mixing portion and a gas vent portion above the liquid mixing portion. The gas vent portion can be above each fluidic channel in communication with the mixing chamber 720. Each fluidic channel in communication with the mixing chamber 720 can interface with the mixing chamber 720 at the bottom portion of the mixing chamber 720 to prevent bubble development and generate a rising fluid level that pushes bubbles to the gas vent portion. In an embodiment, the mixing chamber 720 includes a hydrophobic surface that repels aqueous liquid away from the gas vent portion. Thus, the hydrophobic surface can protect against the extracted nucleic acid mixture portion or amplification reagents from entering or being retained in the gas vent portion. The hydrophobic surface can function as a barrier separating the liquid mixing portion and the gas vent portion. The hydrophobic surface can have non-uniform geometries, heights, levels, and/or areas on the mixing chamber surface. Alternatively, the hydrophobic surface can be uniform.

The extracted nucleic acid mixture portion and the amplification reagents are provided to and mixed in the liquid mixing portion of the mixing chamber 720 to obtain an amplification mixture. Using features discussed above, the mixing chamber 720 can be configured to disrupt the laminar flow of the extracted nucleic acid mixture portion and the amplification reagents as they enter the mixing chamber 720. Laminar flow disruption can cause mixing of the amplification reagents and the extracted nucleic acid mixture portion to obtain the amplification mixture. Gas, such as air, released during mixing of the extracted nucleic acid mixture portion and the amplification reagents can be released from the liquid mixing portion to the gas vent portion of the mixing chamber 720. From the gas vent portion, gas can be released from the microfluidic cartridge 700 though a channel in fluid communication with the mixing chamber 720. The fluidic channel for gas release can be a dedicated channel for this purpose or can be a non-exclusive channel that is used for other purposes. A gas vent outlet can be at the end of the fluidic channel to allow the gas to escape into the environment outside the microfluidic cartridge 700. By venting gas, the mixing chamber 720 can protect against bubbles being present in the amplification mixture during further processing of the sample. The mixing chamber 720 is in fluid communication with the amplification chamber 730.

The amplification chamber 730 is configured for nucleic acid amplification. In embodiments, the amplification chamber 730 is used to perform PCR. To perform PCR, the amplification chamber 730 can be configured for thermal cycling from an amplification thermal module 740. In an embodiment, the amplification thermal module 740 includes a heating unit configured to perform non-contact or contact heating. As an example, the heating unit is an infrared light source for non-contact heating. The amplification thermal module 740 can include a temperature sensing unit. In an embodiment, the temperature sensing unit is an infrared pyrometer. To improve pyrometer sensing accuracy, the amplification chamber 730 can include a thinner portion for infrared pyrometer measurements. The infrared pyrometer measurements at the thinner portion can more accurately reflect the temperature of liquid within the amplification chamber 730. Thermal cycling requires cooling. Thus, the amplification chamber 730 can be configured through material choice to perform rapid cooling when not being heated. In such embodiments, the amplification thermal module 740 does not need a cooling unit to cool the amplification chamber 730. Alternatively, the amplification thermal module 740 can include a cooling unit to perform cooling. As an example, the cooling unit is a cooling fan. In another embodiment, the cooling unit is a compressed air outlet.

During operation, the amplification mixture is provided to the amplification chamber 730. In embodiments, the amplification mixture provided to the amplification chamber 730 has a volume of from about 100 μl to about 5 such as from about 500 μl to about 1.5 μl or about 1 μl. The amplification mixture can have laminar flow as it is provided to the amplification chamber 730 from a fluidic channel exiting the mixing chamber 720. In the amplification chamber 730, the amplification mixture is placed under reaction conditions to amplify template nucleic acid regions (sequences). As an example, the amplification mixture is thermal cycled to perform PCR. During amplification, the amplified nucleic acids can be tagged with labels, such as fluorescent labels. After amplification, the resulting amplified nucleic acid mixture is available for further processing.

Figure 8:
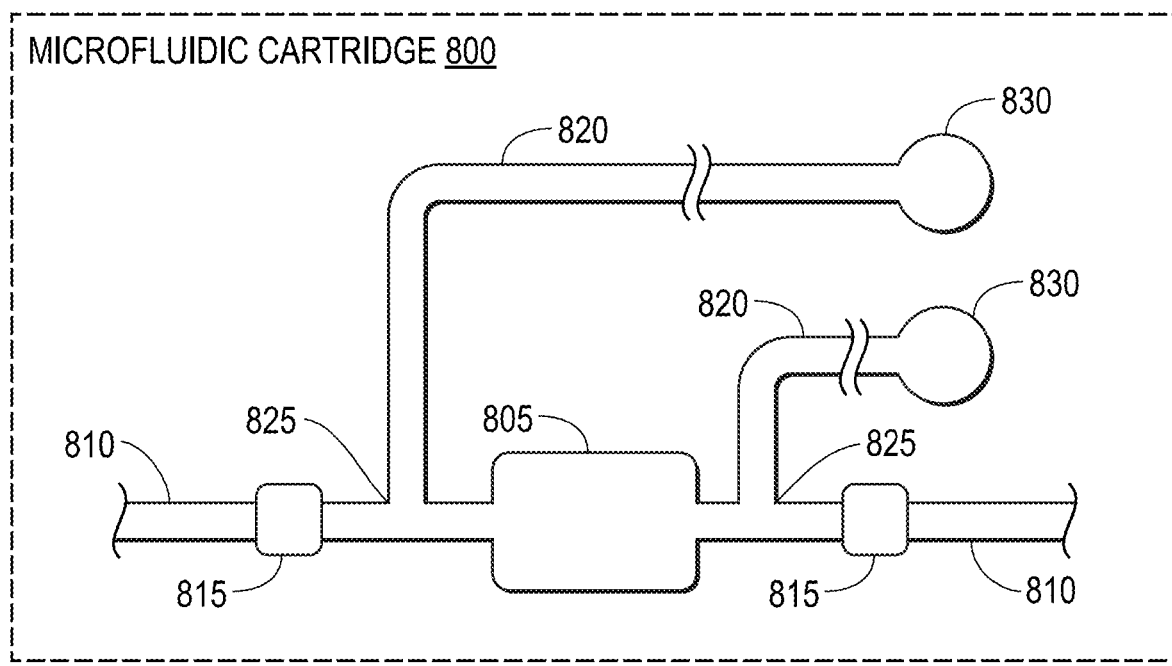
FIG. 8 shows exemplary features of a loadable reservoir.

FIG. 8 shows exemplary features of a loadable reservoir that can be included within a microfluidic cartridge 800. As shown, the microfluidic cartridge 800 includes a reagent reservoir 805 that can be loaded with a reagent solution for performing nucleic acid analysis. The reagent reservoir 805 can be configured to hold any of extraction, amplification, and separation reagents. For example, the reagent reservoir 805 is an amplification reagent reservoir as discussed above. The reagent reservoir 805 is in fluid communication with one or more fluidic channels 810 that lead to other portions of a fluidic network of the microfluidic cartridge 800. One or more (e.g., two) seals 815 are positioned in the one or more (e.g., two) fluidic channels 810 to block the reagent solution from entering or prematurely entering other portions of the fluidic network. The seals 815 can be non-reusable (one-time) or reusable seals and each seal 815 can be of a different type. In embodiments, the seals 815 are frangible seals that can be broken by pressure supplied from a pressure module of a nucleic acid analyzer. The seals 815 can be broken in order to move the reagent solution to another portion of the fluidic network of the microfluidic cartridge 800 and/or to bring the reagent solution under hydrodynamic control of a pressure module of a nucleic acid analyzer. The microfluidic cartridge 800 further includes one or more (e.g., two) bypass fluidic channels 820 in fluid communication with the reagent reservoir 805. The bypass fluidic channels 820 merge with the fluidic channels 810 at junctions 825. A port 830 is in fluid communication with each bypass channel 820 at the other end of the bypass channel 820. One of the ports 830 can be designated as a filling port and the other of the ports 830 can be designated as a gas outlet. At least the filling port 830 can be configured to be fluidically coupled to an off-cartridge store of the reagent solution to be loaded in the reagent reservoir 805.

The reagent reservoir 805 can be loaded with the reagent solution by providing the reagent solution to the reagent reservoir 805 through one of the ports 830 and the associated bypass fluidic channel 820. Gas (e.g., air) present in the reagent reservoir 805 (and the filling port 830 and the associated bypass channel 820) that is displaced during loading of the reagent solution can be expelled out of the reagent reservoir 805 through the other bypass fluidic channel 820 and the associated gas outlet port 830. The gas outlet port 830 can be open to the environment outside the microfluidic cartridge 800 during reagent loading to permit gas to be expelled from the microfluidic cartridge 800. After loading, a sealing member (not shown), such as an adhesive film, can be placed over the ports 830 to protect against contamination. The sealing member can be air-permeable, but not liquid-permeable. The sealing member can be hydrophobic. In embodiments, the sealing member is made from a pressure-sensitive adhesive (PSA) polymer.

Figure 9:
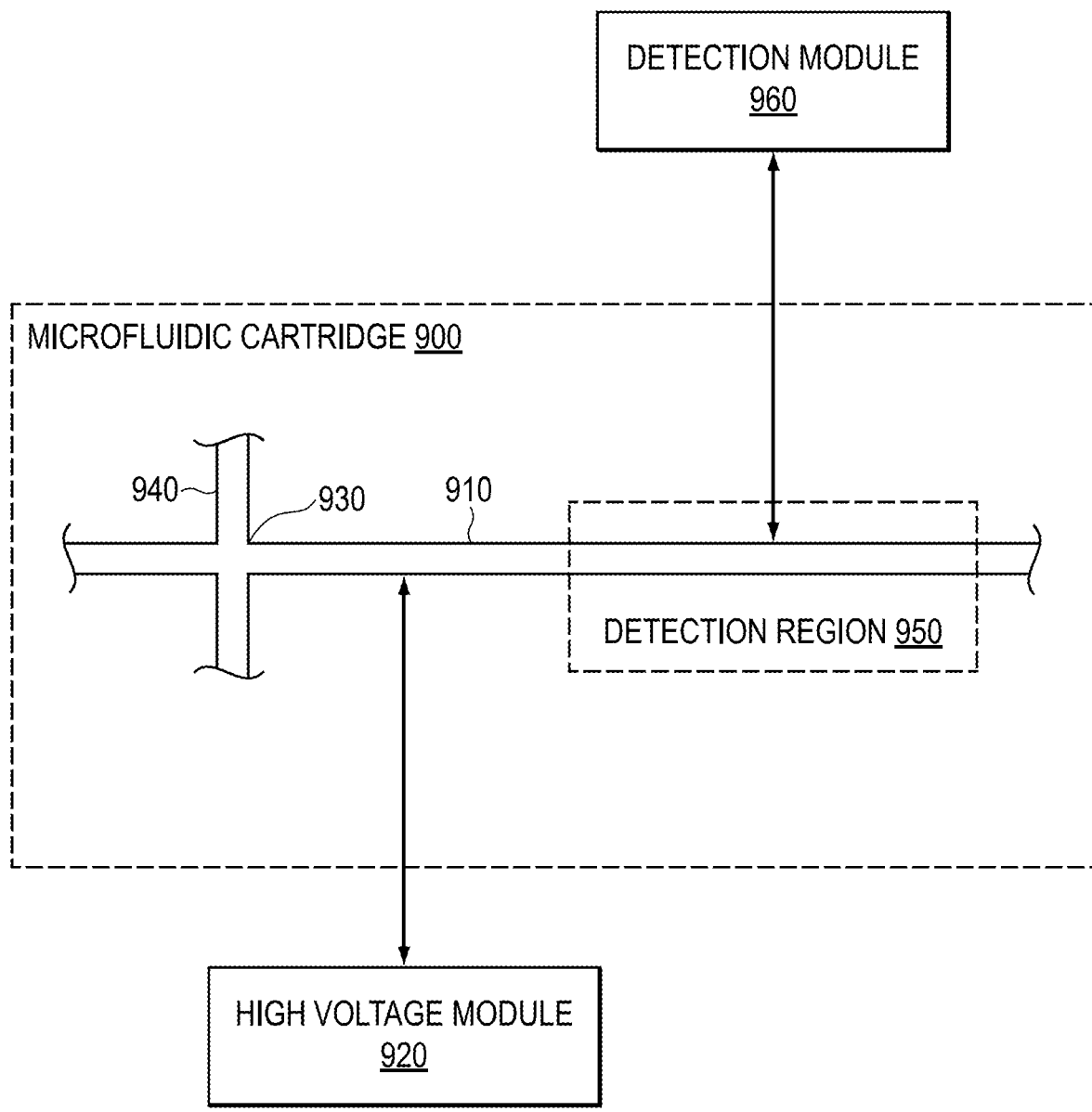
FIG. 9 shows exemplary features for performing nucleic acid separation.

FIG. 9 shows exemplary features for performing nucleic acid separation that can be included within a microfluidic cartridge 900. The on-cartridge features include a separation channel 910. The separation channel 910 can be filled with, for example, a sieving polymer matrix. The sieving polymer matrix can be formed by providing a sieving polymer to the separation channel 910 before nucleic acids are provided to the separation channel 910 for separation. In an embodiment, a nucleic acid mixture, such as a portion of an amplified nucleic acid mixture, can be provided to the separation channel 910. A high voltage module 920 applies high voltage to electrodes (not shown) on the microfluidic cartridge 900 to induce electro-kinetic injection and/or electrophoretic separation. As shown, a T-junction 930 is provided at the beginning of the separation channel 910. The nucleic acid mixture can be provided to the beginning of the separation channel 910 by electro-kinetic injection of a portion of the amplified nucleic acid mixture through a fluidic channel 940.

Before being provided to the separation channel 910, the nucleic acid mixture (or a portion thereof) can be diluted or mixed with one or more separation reagent solutions, such as any of an internal control solution, a dilution solution, and a buffer solution, to improve nucleic acid separation. The nucleic acid mixture (or portion thereof) can be mixed with the separation reagents in a ratio of about 1:1 to about 1:100, such as from about 1:10 to about 1:30 or about 1:15, depending on the concentrations of the reagents. As an example, the nucleic acid mixture can be mixed with an internal control solution that includes an internal lane standard (ILS). The ILS can be used to better ensure accurate size measurements of the nucleic acid fragments. The ILS includes nucleic acids of known size that are used as controls. The internal control solution can also include formamide for denaturing nucleic acids to promote separation. As another example, the nucleic acid mixture can be mixed with an aqueous dilution solution to reduce the ionic strength of the nucleic acid mixture. In order to detect and analyze the separated nucleic acid fragments, the nucleic acid fragments can be labeled prior to separation. The nucleic acid fragments can be labeled during amplification, such as with fluorescent labels. Alternatively, the nucleic acid fragments can be labeled after amplification but prior to separation by mixing the nucleic acid fragments with a dye, such as an intercalating dye (e.g., ethidium bromide). The dye can be included in the internal control solution or another solution.

Once the nucleic acid mixture, such as a portion of an amplified nucleic acid mixture mixed with separation reagents, is provided to the separation channel 910, the nucleic acid fragments within the mixture can be separated. In an embodiment, nucleic acid separation is performed by electrophoresis such that nucleic acid fragments are separated by size. In electrophoresis, the nucleic acid fragments migrate by force of the electric field at different speeds based on the sizes of the nucleic acid fragments. During separation, the separated nucleic acid fragments can be detected through observation of the detection region 950 of the separation channel 910. The detection region 950 can include a detection window configured to enable detection by a laser beam. A detection module 960 is operably coupled to the detection region 950. The detection module 960 can emit a laser beam. The laser beam can be directed to the detection region 950 to excite fluorescent molecules associated with the nucleic acid fragments as they pass through the detection region 950 during nucleic acid separation.

Figure 10:
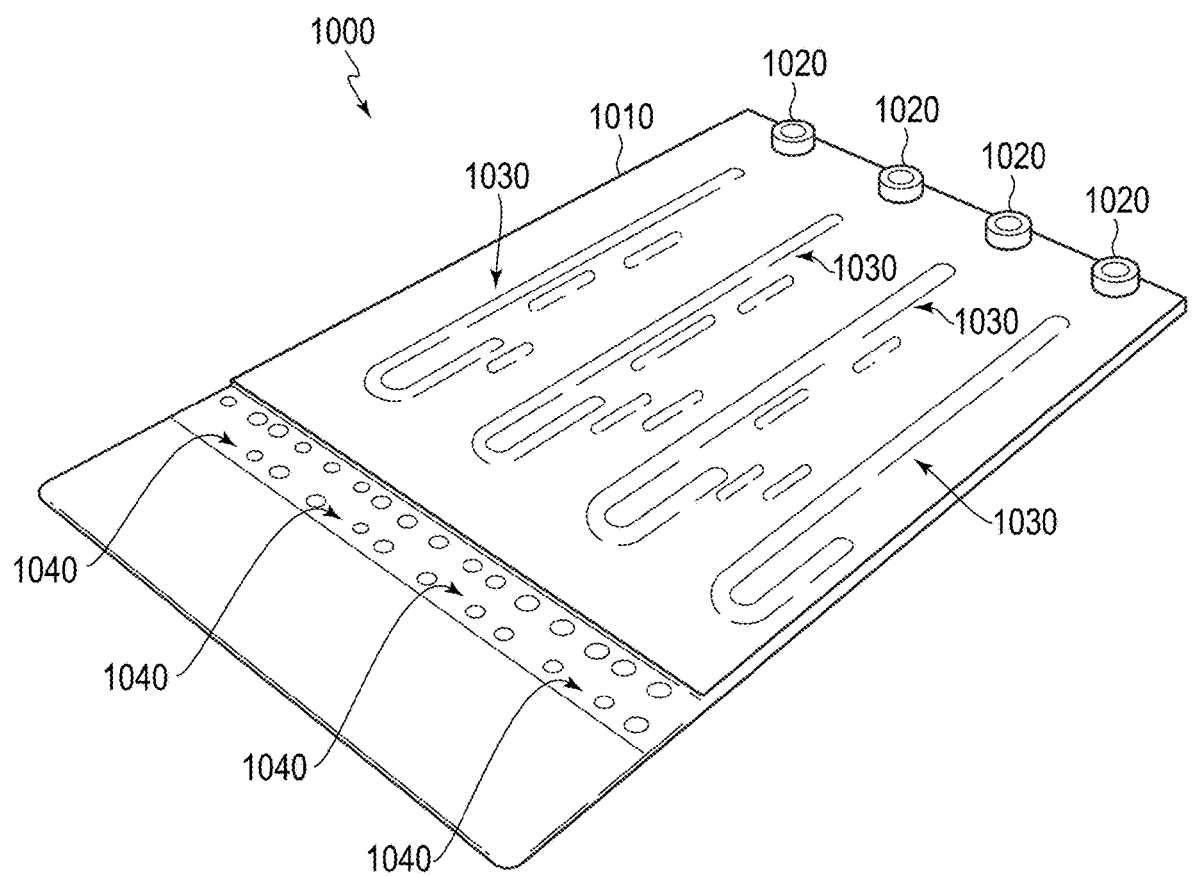
FIG. 10 shows an exemplary microfluidic cartridge and an exemplary sealing layer to be applied over at least a major portion of the microfluidic cartridge.

FIG. 10 shows an exemplary microfluidic cartridge 1000 and an exemplary sealing layer 1010 to be applied over at least a major portion of the microfluidic cartridge 1000. Broadly, the microfluidic cartridge can include one or more sample inputs 1020, one or more fluidic networks 1030, and one or more vent port areas 1040. As shown, four sample inputs 1020, fluidic networks 1030, and vent port areas 1040 are defined in the microfluidic cartridge 1000. The sample inputs 1020 can be configured for fluidic coupling of sample acceptors. The fluidic network 1030 can include features for performing any of nucleic acid extraction, amplification, and separation. Each vent port area 1040 includes a plurality of vent ports that can be configured for coupling to a pressure module of a nucleic acid analyzer to provide hydrodynamic control over liquid within the fluidic networks 1030 during nucleic acid analysis.

The sealing layer 1010 is applied over at least the fluidic networks 1030 of the microfluidic cartridge 1000 to provide a top layer over fluidic network features, including channels, reservoirs, and chambers. In embodiments, the sealing layer 1010 is applied over the sample inputs 1020 and the fluidic networks 1030 or over the entirety of the microfluidic cartridge 1000. The sealing layer 1010 can be in the form of a film and can be pliable. The sealing layer 1010 can be adhered to the surface of the microfluidic cartridge 1000 by heat-driven lamination. In an embodiment, there are two sealing layers that are respectively applied over the top and the bottom of the microfluidic cartridge 100.

The pressure module of the nucleic acid can be configured to independently apply positive and/or negative pressure to individual vent ports to effectuate hydrodynamic movement in performing nucleic acid analysis. Each vent port can be in fluid communication with a discrete feature in the fluidic network 1030 such as to control hydrodynamic movement of liquid with respect to such feature. The vent ports can be coupled to the pressure module through a micro-to-macro interface. The vent ports can be covered with a covering (not shown) that permits the passage of gas (e.g., air) while preventing the passage of liquid. As shown, the vent port areas 1040 are provided on one side of the microfluidic cartridge 1000. Although not necessary, this can generally provide minimal complexity in the micro-to-macro interface with the pressure module of the nucleic acid analyzer. The sealing layer 1010 can also be used to form frangible seals within the fluidic networks 1030.

Figure 11:
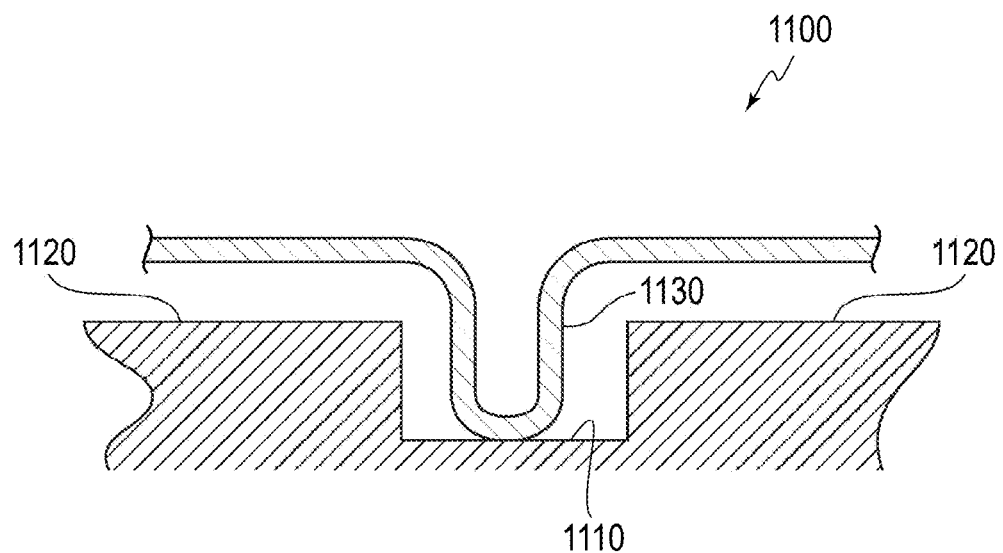
FIG. 11 shows an exemplary frangible seal within a fluidic channel.

FIG. 11 shows an exemplary frangible seal 1100. As shown, the frangible seal 1100 is formed from a depression 1110 defined within a fluidic channel 1120. The depression 1110 has a depth that is greater than the depth of the fluidic channel 1120. However, the depression 1110 can have a depth that is less than the depth of an adjacent reagent reservoir or other chamber. A sealing layer portion 1130 is extended into the depression 1110 such that the sealing layer portion 1130 contacts and is adhered to the base of the depression 1110.

The frangible seal 1100 can be configured to have a predetermined resistance against fluid flow. Fluid flow resistance can be determined by the depth and width of the depression 1110. In general, the frangible seal 1110 has weaker fluid flow resistance as the depression 1110 is made deeper and has greater fluid flow resistance as the depression 1110 is made shallower. A shallower depression 1110 does not stretch the sealing layer portion 1130 as much as a deeper depression 1110 and, thus, a shallower depression 1110 provides more resistance to fluid flow. In embodiments, a fluidic network of a microfluidic cartridge includes frangible seals 1100 having different fluid flow resistances.

For instance, the fluidic network can have frangible seals 1100 that have two different fluid flow resistances. A depression 1110 having a depth of about 40 µm to about 50 µm can be used to form frangible seals 1100 that have sufficient fluid flow resistance to border reagent reservoirs to protect against reagent solution from entering other portions of the fluidic network in the course of loading reagents or operating the microfluidic cartridge until the frangible seals 1100 are intentionally broken by pressure applied by a pressure module. A depression 1110 having a depth of about 15 µm to about 25 µm can be used to form a frangible seal 1100 having a greater fluid flow resistance. The frangible seal 1100 of greater fluid flow resistance can be used in places along the fluidic network where another actuation feature under the control of the pressure module, such as a reusable actuation feature (e.g., a valve), is in close proximity to the location for the frangible seal 1100 of greater fluid flow resistance. A frangible seal 1100 of greater fluid flow resistance is provided in such places to protect against inadvertent seal breakage during operation of the actuation feature.

During operation of the microfluidic cartridge, the frangible seal 1100 can be broken by providing positive or negative pressure of sufficient force through the fluidic channel 1120. Such pressure can cause the sealing layer portion 1130 to detach from the base of the depression 1110. One detached, the sealing layer portion 1130 does not normally reattach to the depression 1110 once pressure is removed. Thus, once broken, the frangible seal 1100 is not automatically reconstituted and represents a one-time actuation feature of the microfluidic cartridge.

Figure 12:
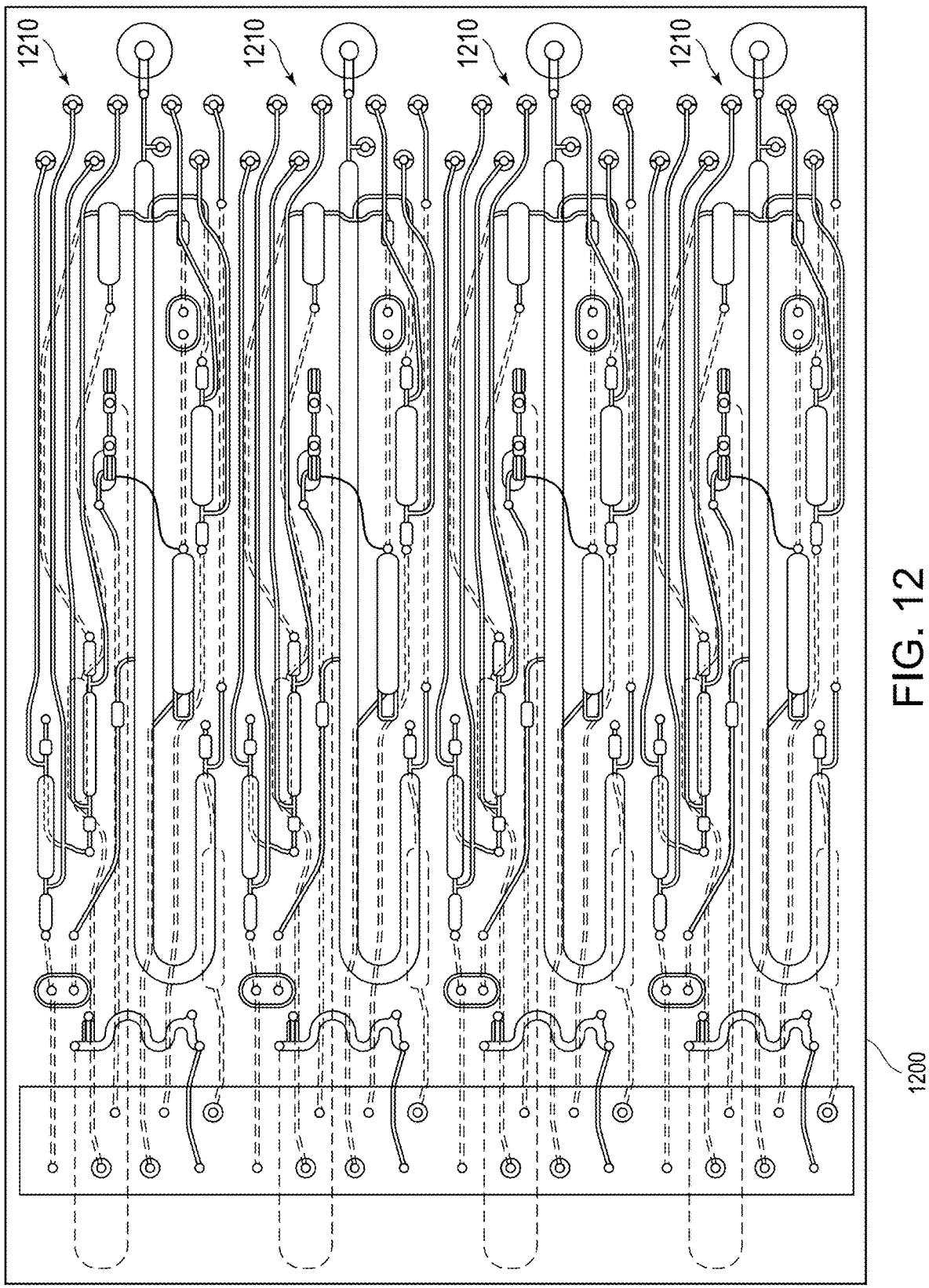
FIG. 12 is a schematic of an exemplary microfluidic cartridge that combines various features for nucleic acid extraction, nucleic acid amplification, and nucleic acid separation.

FIG. 12 shows a schematic of an exemplary microfluidic cartridge 1200 that combines various features for nucleic acid extraction, nucleic acid amplification, and nucleic acid separation. The microfluidic cartridge 1200 includes four identical nucleic acid analysis portions 1210, in which a biological sample can be analyzed. Accordingly, the nucleic acid analysis may be performed on four different biological samples in parallel or in tandem. In other embodiments, the microfluidic cartridge 1200 can include more or less nucleic acid analysis portions and may only contain a single nucleic acid analysis portion 1210. However, the incorporation of more than one nucleic acid analysis portion 1210 on a microfluidic cartridge 1200 can improve efficiency and/or convenience. Of course, different biological samples can be individually analyzed in the nucleic acid analysis portions 1210. Alternatively, a biological sample can be divided and nucleic acid analysis performed more than once on the same biological sample. Such redundancy can improve accuracy. Further, there is no requirement that all nucleic acid analysis portions 1210 are identical as, for example, nucleic acid analysis portions 1210 on the microfluidic cartridge 1200 can be configured to perform different types of nucleic acid analyses. Alternatively, the individual nucleic acid analysis portions 1210 may be used to perform analyses on unknown samples, positive control samples, negative control samples, or any combination thereof. For instance, a first nucleic acid analysis portion 1210 can be used to analyze an unknown sample and a second nucleic acid analysis portion 1210 can be used to analyze an allelic ladder.

The cartridge interface module (CIM) is designed to connect to and control a disposable or interchangeable microfluidic cartridge, such as that described in U.S. patent application Ser. No. 13/064,094, which is incorporated in its entirety by reference herein. The microfluidic cartridge is inserted into the CIM and utilized in a user friendly manner without the possibility of instrument or human contamination for DNA identification. The CIM allows for a microfluidic cartridge to be inserted into an opening that guides it to the correct loading area. When a door of the nucleic acid analyzer system is closed, the system locks both the door in place and engages the CIM. When the CIM is engaged, the microfluidic cartridge becomes linked to the instrument, which allows for a DNA identification test to be run. When the testing is completed, the CIM disengages from the microfluidic cartridge and the door is unlocked.

Figure 13:
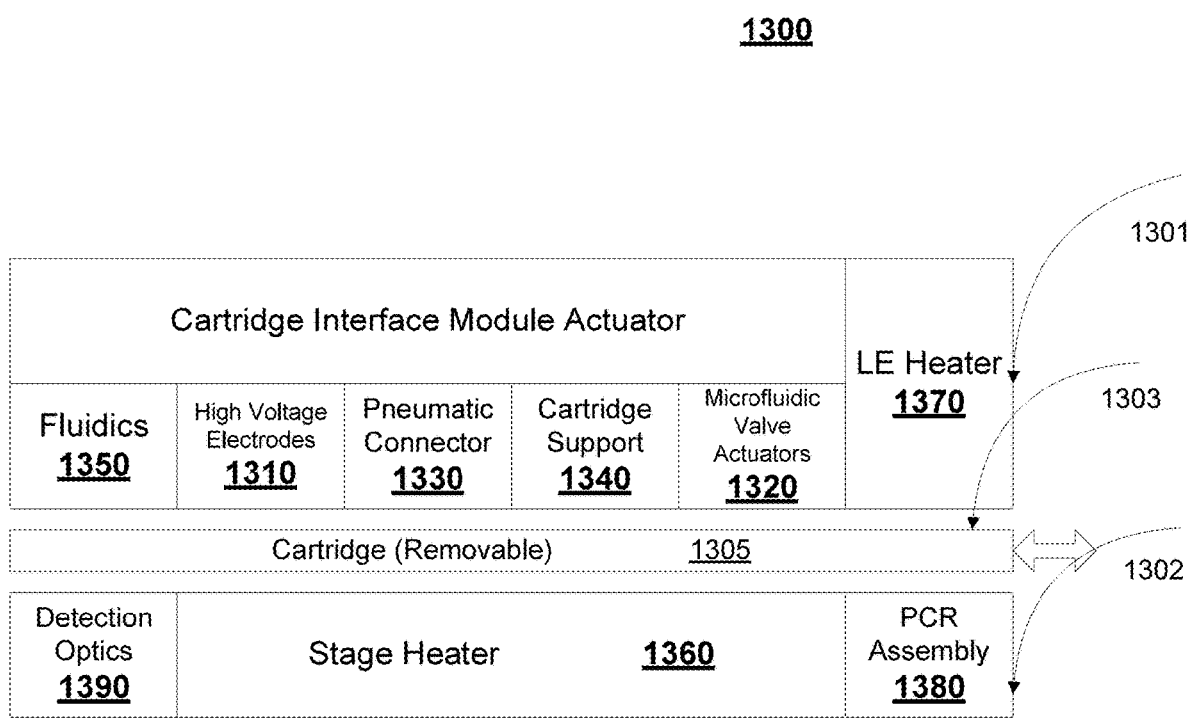
FIG. 13 is an illustration of a cartridge interface module.

FIG. 13 illustrates an exemplary CIM 1300, which includes an upper portion 1301 and a lower portion 1302, and an intervening slot 1303 in which a removable microfluidic cartridge 1305 is inserted and removed. The cartridge 1305 can rest on a metal plate of a stage. On the upper portion 1301, a high voltage electrode component 1310 is illustrated. The high voltage electrode component 1310 provides an automatic connection of high voltage sources directly to microfluidic channels on the cartridge 1305, while maintaining a fluidic seal of the cartridge 1305. In contrast, some conventional systems insert electrodes into the cartridge.

A microfluidic valve actuator component 1320 is also illustrated in FIG. 13. The microfluidic valve actuator component 1320 seals the cartridge 1305 to the CIM 1300. A pneumatic connector component 1330 is also illustrated in FIG. 13, which provides a contamination-proof fluidic seal to the cartridge 1305 from the rest of the system. Some conventional systems require replacement of direct fluid connections after each test since the DNA from a previous test can contaminate the results of later tests. Embodiments described herein for a pneumatic connector component 1330 provide a contamination-free environment for continuous testing without changing out any parts.

A cartridge support component 1340, illustrated in FIG. 13 provides the cartridge 1305 with structural support. The embodiment described herein provides a CIM 1300 to be used in conjunction with a removable plastic cartridge 1305. The cartridge support component 1340 provides support to the cartridge 1305, which allows for much greater forces to be applied to the cartridge 1305. The combination of pneumatic connections, cartridge supporting structures, and mechanical microfluidic valve actuators are configured in the CIM 1300 to reduce or eliminate the possibility of cross contamination.

FIG. 13 further illustrates a fluidics component 1350, which directs a pressure source to the cartridge 1305. The embodiment of the CIM 1300 directs flow from four or more pressure sources to twenty four or more ports on the microfluidic cartridge 1305. This provides a fluid movement on a microfluidic scale to drive the fluid through a test, while also providing design flexibility to optimize the flow characteristics. A stage heater component 1360 on the lower portion 1302 of the CIM 1300 uniformly heats the cartridge 1305. A liquid extraction heater component 1370 on the upper portion 1301 of the CIM 1300 works in conjunction with the fluidics component 1350 to initiate and support a simplified extraction analysis process in the microfluidic cartridge 1305 with reduced cross contamination. The liquid extraction heater component 1370 supports a fully integrated liquid-based extraction, which allows DNA extraction with a limited control system and less complexity than a solid phase extraction process used in some conventional processing. Solid phase extraction uses metallic beads to extract the DNA from the cells that need to be processed, washed, and removed. In contrast, liquid phase extraction uses an enzyme to extract the DNA, which only requires the aliquot to be thermo-cycled. This greatly simplifies the overall system.

A PCR assembly component 1380, illustrated in FIG. 13, initiates and supports the amplification process in the microfluidic cartridge 1305. The PCR component 1380 utilizes a non-contact infrared thermo-cycling process, which is described below with reference to FIG. 15.

A detection optics component 1390 of the CIM 1300 is also shown in FIG. 13. The detection optics component 1390 and the high voltage electrodes component 1310 work in conjunction in a nucleic acid separation process. The separation process is achieved by utilizing a shorter separation channel within the microfluidic cartridge. For example, an embodiment, a channel of approximately 7 cm is used. Embodiments described herein utilize a microfluidic chip architecture, rather than require an additional sub-assembly to the system to execute the separation process. In some conventional systems that require a separate sub-assembly, the genetic material to be tested is passed from the microfluidic cartridge into the testing instrument. In contrast, embodiments described herein provide a microfluidic chip-based electrophoresis component. The shorter separation channel utilized by the microfluidic chip architecture, together with the pneumatic connections, cartridge supporting structures, and mechanical microfluidic valve actuators in the CIM 1300 reduce or eliminate the possibility of cross contamination from instrument contamination and human intervention. This is made possible by eliminating the need to move the genetic material to be tested from the microfluidic cartridge into a separate sub-assembly.

Figure 14:
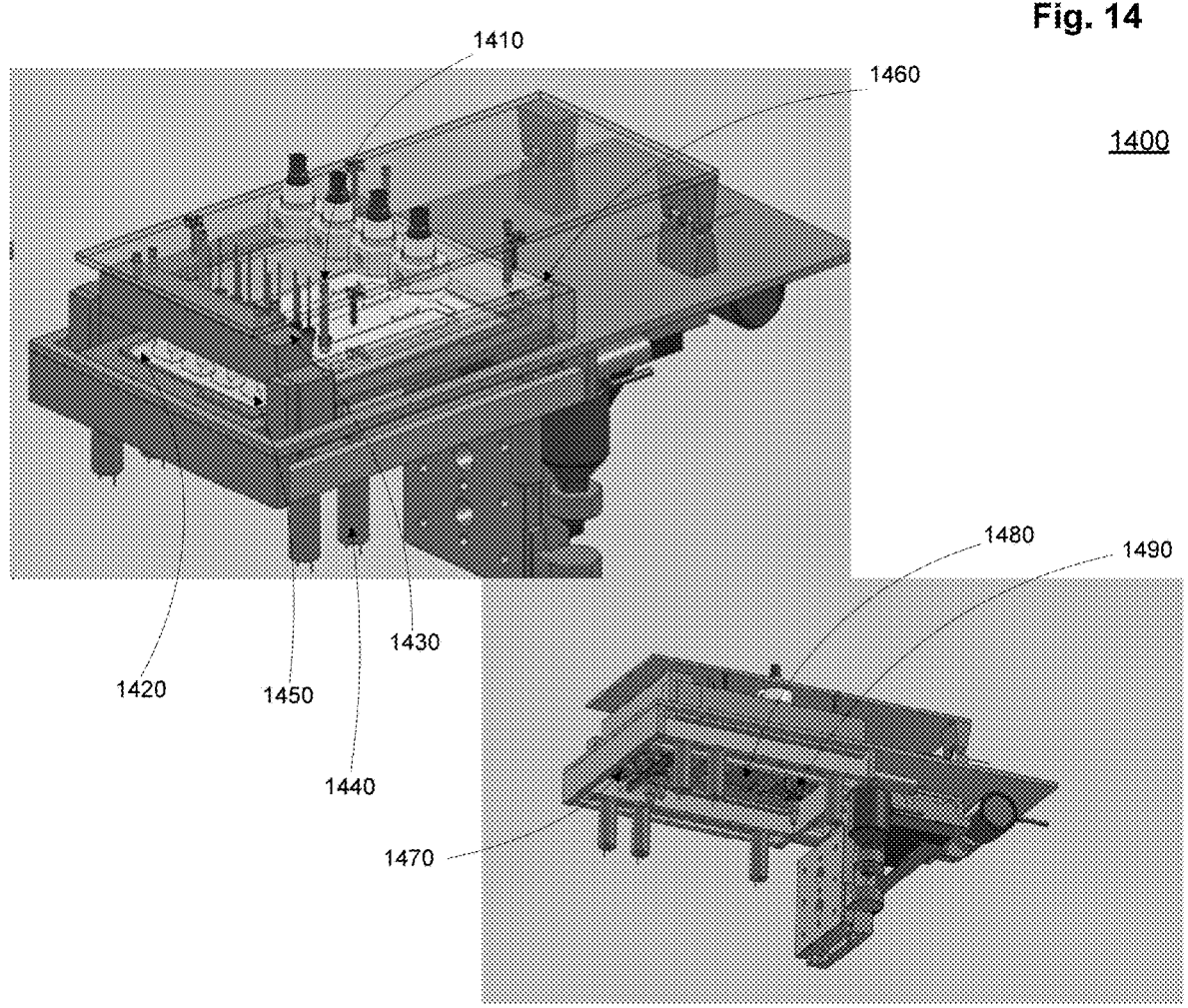
FIG. 14 is a drawing of a cartridge interface module.

FIG. 14 is a drawing which illustrates a top view and a side view of an embodiment of a cartridge interface module 1400. A high voltage electrode 1410 provides a high voltage source directly to the microfluidic channels on a cartridge. The fluidic seal of the cartridge is maintained. A cartridge 1420 is also illustrated. In an embodiment, the cartridge 1420 is removable and disposable, and subsequent cartridges can easily be swapped and inserted for subsequent testing. A fluidics region 1430 directs flow from multiple pressure sources to multiple ports on the microfluidic cartridge 1420. A CIM actuator 1440 seals the system from the inserted cartridge 1420. A pneumatic connector 1450 provides a contamination-proof fluidic seal to the cartridge 1420 from the rest of the system. A cartridge support 1460 provides the cartridge 1420 with structural support. The PCR assembly 1470 provides non-contact infrared thermocycling. A stage heater 1480 uniformly heats the cartridge 1420.

FIG. 14 also illustrates an optical device assembly 1490. In an embodiment, an optical device provides an illuminating path that directs a first input light beam received from a light source to a first separation channel of a microfluidic chip. The first input light beam causes fluorescent labels attached onto DNA fragments in the first separation channel to emit a first fluorescence light. A detecting path collects and directs the first fluorescent light to a first group of optical fibers. A spectrometer receives the first fluorescent light from the optical fibers and detects fluorescent components in the first fluorescent light. Additional embodiments of the optical device assembly 1490 are further described in U.S. patent application Ser. No. 13/273,947, which is incorporated by reference herein in its entireties.

Figure 15:
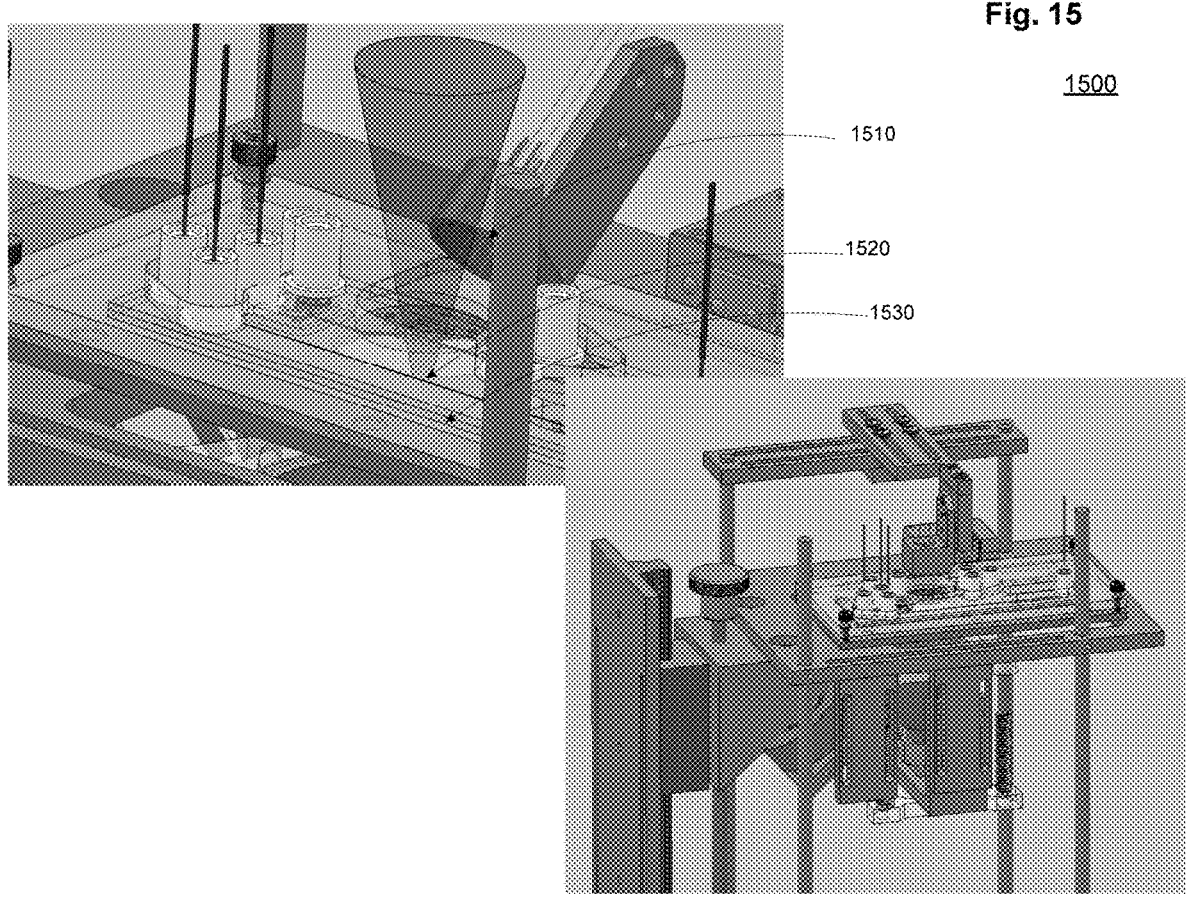
FIG. 15 is a drawing of a pyrometer used with a cartridge interface module.

Referring back to FIG. 13, the PCR component 1380 of the CIM 1300 utilizes complete non-contact nucleic acid amplification processing. An infrared wavelength can be used to heat liquid in the PCR chamber of the microfluidic cartridge. In addition, a non-contact temperature sensor can be used, such as a pyrometer. FIG. 15 illustrates a top view and a side view of a pyrometer 1500 used in conjunction with a nucleic acid analyzer system, according to embodiments described herein. A pyrometer assembly 1510 is positioned above the CIM. An infrared source 1520 is directed towards a cartridge 1530. Other temperature sensors are contemplated by embodiments described herein, in which a non-contact method and system intercept and measure thermal radiation.

The CIM of a nucleic acid analyzer system described herein provides an interface to receive a removable microfluidic cartridge, containing all needed reagents and samples, and provide all needed functionality to the microfluidic cartridge for nucleic acid extraction, amplification, and separation. The CIM has several advantages and features, including but not limited to a user-friendly cartridge input, a liquid extraction heater and feedback, a stage heater and feedback, an integrated microfluidic control, integrated microfluidic valve mechanics, a cartridge support, a PCR cycling apparatus, a microfluidic chip based electrophoresis apparatus, contamination-free pneumatic connections, and a modular design for ease of servicing.

FIG. 16 is a flow diagram illustrating an exemplary process 1600 of analyzing a biological sample for DNA analysis. A removable microfluidic cartridge is received into a cartridge interface module (CIM) of a nucleic acid analyzer system in step 1610. An extraction of nucleic acids from the biological sample contained within the removable microfluidic cartridge is initiated and supported, via a fluidics component of the CIM while engaged with the removable microfluidic cartridge in step 1620. An amplification of the extracted nucleic acids is initiated and supported, via a polymerase chain reaction (PCR) assembly component of the CIM while engaged with the removable microfluidic cartridge in step 1630. A separation of the amplified nucleic acids into nucleic acid fragments is initiated and supported, via a high voltage electrodes component of the CIM, while engaged with a separation channel of the removable microfluidic cartridge in step 1640. An input light beam is directed to a separation channel for detection and collection of the nucleic acid fragments, via a detection optics component of the CIM in step 1650. The CIM is configured to integrate with a microfluidic chip architecture while engaged with the removable microfluidic cartridge for execution of the extraction, amplification, and separation of the biological sample within the removable microfluidic cartridge.

While the invention has been described in conjunction with the specific exemplary embodiments thereof, it is evident that many alternatives, modifications, and variations will be apparent to those skilled in the art. Accordingly, exemplary embodiments as set forth herein are intended to be illustrative, not limiting. There are changes that may be made without departing from the spirit and scope of the invention.

What is claimed:

1. A cartridge interface module (CIM), configured to engage with a removable microfluidic cartridge in a nucleic acid analyzer system, the CIM comprising:
    a fluidics component disposed in an upper portion of the CIM, the upper portion of the CIM being separated from a lower portion of the CIM by an intervening slot configured to guide the removable microfluidic cartridge to a loading area, wherein the fluidics component is configured to initiate and support a liquid extraction of nucleic acids from a biological sample contained in the removable microfluidic cartridge by directing fluid flow from a plurality of pressure sources to a plurality of pressure ports on the removable microfluidic cartridge;
    a polymerase chain reaction (PCR) assembly component disposed in the lower portion of the CIM, wherein the PCR assembly component is configured to initiate and support amplification of extracted nucleic acids via a non-contact infrared thermo-cycling mechanism configured to heat liquid;
    a high voltage electrodes component disposed in the upper portion of the CIM to provide an automatic connection of a high voltage source directly to microfluidics channels on the removable microfluidic cartridge while maintaining a fluidic seal of the removable microfluidic cartridge, wherein the high voltage electrodes component is configured to initiate and support separation of the amplified nucleic acids into nucleic acid fragments in a separation channel of the removable microfluidic cartridge; and
    a detection optics component disposed in the lower portion of the CIM, wherein the detection optics component is configured to detect labeled nucleic acid fragments and work in conjunction with the high voltage electrodes component in the separation of the amplified nucleic acids,
    wherein the CIM is configured to integrate with a microfluidic chip architecture of the removable microfluidic cartridge to run a DNA identification test when inserted in the CIM, the microfluidic chip architecture integrating with the CIM for execution of the extraction, amplification, and separation of the biological sample within the removable microfluidic cartridge, the CIM providing predetermined functionality to the microfluidic cartridge for nucleic acid extraction including the non-contact infrared thermo-cycling.

2. The CIM of claim 1, wherein the separation channel is integrated with the microfluidic chip architecture.

3. The CIM of claim 1, wherein genetic material from the biological sample is not transferred out of the removable microfluidic cartridge during analysis of the biological sample.

4. The CIM of claim 1, further comprising:
one or more pneumatic connections within the CIM, configured to engage with the removable microfluidic cartridge.

5. The CIM of claim 1, further comprising:
one or more cartridge supporting structures within the CIM that are configured to engage with the removable microfluidic cartridge.

6. The CIM of claim 1, further comprising:
one or more mechanical microfluidic valve actuators within the CIM that are configured to engage with the removable microfluidic cartridge.

7. The CIM of claim 1, wherein the non-contact mechanism comprises a pyrometer temperature sensor.

* * * * *